United States Patent
Massimo, Sr.

(10) Patent No.: US 6,494,489 B2
(45) Date of Patent: *Dec. 17, 2002

(54) LATENT FINGERPRINT LIFTING AND RECORDATION DEVICE

(75) Inventor: John M. Massimo, Sr., Bradenton, FL (US)

(73) Assignee: Pro-Lift Fingerprint Collection System, Inc., Bradenton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/864,751

(22) Filed: May 24, 2001

(65) Prior Publication Data

US 2002/0027360 A1 Mar. 7, 2002

Related U.S. Application Data

(63) Continuation-in-part of application No. 09/653,067, filed on Sep. 1, 2000, now Pat. No. 6,260,885.

(51) Int. Cl.$^7$ .................................................. B42D 15/00
(52) U.S. Cl. ........................... 283/68; 283/78; 283/101; 382/124
(58) Field of Search ............................ 283/68, 69, 74, 283/75, 78, 115, 100, 103, 104; 382/124; 462/84; 206/807

(56) References Cited

U.S. PATENT DOCUMENTS

| | | | | |
|---|---|---|---|---|
| 1,607,946 A | * | 11/1926 | Crosskey | |
| 2,007,589 A | * | 7/1935 | Williams | |
| 2,048,879 A | * | 7/1936 | Moran | |
| 3,419,287 A | * | 12/1968 | Rudie | |
| 3,694,240 A | | 9/1972 | Miller et al. | |
| 3,867,164 A | * | 2/1975 | Orlando et al. | 117/5 |
| 3,959,884 A | * | 6/1976 | Jordan et al. | 33/1 BB |
| 4,325,570 A | * | 4/1982 | Estrada | 283/7 |
| 4,706,600 A | | 11/1987 | Mason et al. | |
| 5,078,426 A | | 1/1992 | Reardon | |
| 5,114,188 A | | 5/1992 | Koch | |
| 5,281,293 A | | 1/1994 | Frame et al. | |
| 5,390,680 A | * | 2/1995 | Brenner | 128/779 |
| 6,260,885 B1 | * | 7/2001 | Massimo, Sr. | 283/68 |

OTHER PUBLICATIONS

Ace Fingerprint Equipment Laboratories, Inc. Catalog, p. 11.
Lynn Peavey Company 1999 Crime Scene Investigator's Product Guide, p. 21.
Sirchie Fingerprint Laboratories Catalog, p. 91.
ODV Fingerprinting & Crime Scene Catalogue.
Lightning Powder Company, Inc. Catalog, p. 10.

* cited by examiner

Primary Examiner—A. L. Wellington
Assistant Examiner—Monica Carter
(74) Attorney, Agent, or Firm—Charles J. Prescott

(57) ABSTRACT

A latent fingerprint lifting and recordation device of the type which provides a permanent and official fingerprint document. The device includes a flexible transparent latent fingerprint lifting sheet having one adhesive surface and a flat opaque somewhat thicker, less flexible sheet defining a perimeter frame and a removable central area which defines a protective cover, the perimeter frame being substantially similar in size and shape to that of, and adhered in generally coextensive fashion on one surface thereof against the adhesive side of the fingerprint lifting sheet. When the transparent fingerprint lifting sheet, with the perimeter frame adhesively attached thereto, is separated from the protective cover, an imaged latent fingerprint may be lifted and recorded on the adhesive surface. The latent fingerprint thereafter is protectively sandwiched for viewing through the transparent sheet when the protective cover is adhesively reattached to the adhesive surface to form a permanent fingerprint document. A preferred aspect of this invention is derived from the reversing of the protective cover which carries printed indicia on an obverse surface thereof.

5 Claims, 3 Drawing Sheets

LATENT FINGERPRINT LIFTING AND RECORDATION DEVICE

This is a continuation-in-part of U.S. patent application Ser. No. 09/653,067 filed Sep. 1, 2000. Now U.S. Pat. No. 6,260,885.

BACKGROUND OF THE INVENTION

1. Scope of Invention

This invention relates generally to the field of taking and recording fingerprints, and more particularly to a device for the lifting and recordation of latent fingerprints into a permanent document for later official use.

2. Prior Art

A The lifting of latent fingerprints is traditionally done in its most economical fashion by using a length of one-sided adhesive transparent packing tape. A length of such tape is s imply applied directly over the latent print once it has bee n identified and powder treated or imaged for enhanced viewability by then simply pressing the adhesive surface of the tape segment directly atop the fingerprint and thereafter simply removing the tape carrying with it the fingerprint image attached thereto.

The lifted latent fingerprint is then typically adhesively attached to a stiff opaque card and labeled appropriately. However, the end product, which may be depended upon for use at trial and the like, has a generally unprofessional and inconsistent appearance and, for the truly professional law enforcement agents, further mounting and preparation into a more formal document for such use is desirable.

A device for lifting and processing latent fingerprints has been invented by Frame and is shown in U.S. Pat. No. 5,281,293. This device is directed to applying fingerprint lifting tape to imaged residues via an arcuate base member with a handle means for providing a rocking motion to the arcuate base member while it carries a releasably attachable length of lifting tape applied to the outside of the arcuate member.

Mason, in U.S. Pat. No. 4,706,600 teaches another kit for making sets of transparent fingerprints utilizing a differential adhesion concept, the device including a backing adhesive sheet, a centrally positioned transparent adhesive print strip and a protective cover.

Another fingerprint recording device has been invented by Reardon as disclosed in U.S. Pat. No. 5,078,426 teaching a protected area for the recording and preservation of a latent fingerprint attached over a portion of an identifying card and providing for the removal of the fingerprint for further forensic and verification processes.

In U.S. Pat. No. 5,114,188, Koch discloses a fingerprinting system and method for taking and developing fingerprints in a formal setting wherein the subjects' fingers are cleansed of dirt and chemicals. The fingerprint is recorded on a layer of adhesive adhered to a sheet of transparent material which is then developed by making a copy of the sensitized surface by back reflecting radiant energy.

A method of taking limb impressions is disclosed by Brenner in U.S. Pat. No. 5,390,680 wherein the impression of a limb such as a foot or hand may be prepared for mail order or catalog sales for shoes and gloves and shoe inserts without the need for direct sizing.

An unpatented device shown in current catalogs such as those distributed by Sirchie Fingerprint Laboratories, ODV Fingerprinting and Crime Scene Catalogue, Lightning Powder Company, Inc., and Ace Fingerprint Equipment Laboratories, Inc., as a latent fingerprint device is generally characterized as having a transparent fingerprint lifter hingedly attached along one common margin to an underlying rigid opaque panel, the fingerprint, once taken onto the adhesive surface of either the opaque panel or the transparent sheet, being preserved after the two are resandwiched back together. Although listed in the above-referenced catalogs, this unpatented device has clearly not made its presence well known in the marketplace as applicant, who has been associated with law enforcement for nearly three decades, has never encountered this device in the field of crime investigation.

The following prior art patents are also known:

U.S. Pat. No. 1,607,946 to Crosskey
U.S. Pat. No. 2,006,744 to Pierce
U.S. Pat. No. 2,007,589 to Williams
U.S. Pat. No. 2,048,879 to Moran
U.S. Pat. No. 3,419,287 to Rudie
U.S. Pat. No. 3,694,240 to Miller et al.
U.S. Pat. No. 3,867,164 to Orlando et al.
U.S. Pat. No. 3,959,884 to Jordan et al.
U.S. Pat. No. 4,325,570 to Estrada The present invention provides an economical to manufacture and easily useable latent fingerprint lifting and recordation device which not only facilitates the easy lifting of a latent fingerprint, but also provides an immediately available permanent recordation document of the latent print which is professional in appearance for use in both legal and financial verification settings.

BRIEF SUMMARY OF THE INVENTION

This invention is directed to a latent fingerprint lifting and recordation device of the type which provides a permanent and official fingerprint document. The device includes a flexible transparent latent fingerprint lifting sheet having one adhesive surface thereof and a flat opaque less flexible two-part sheet defining a perimeter frame and a removable central area which defines a protective cover. The frame is substantially similar in size and shape to that of, and adhered in generally coextensive fashion on, an obverse surface thereof against the adhesive side of the fingerprint-lifting sheet. When the cover is separated from the transparent fingerprint-lifting sheet, with the frame still adhesively attached thereto, a fingerprint may be lifted onto the exposed adhesive surface. After an imaged latent fingerprint is lifted, the latent fingerprint is protectively sandwiched for viewing through the transparent sheet by reattaching the unmarked reverse side of the cover to the adhesive surface to form a permanent fingerprint document, the obverse surface of the cover having a printed area for entering information related to each latent fingerprint taken.

It is therefore an object of this invention to provide a latent fingerprint lifting and recordation device formed as a unit which may be easily temporarily separable for lifting a latent fingerprint and then recombined into a single professional document recording the fingerprint for later professional, legal and financial use as required.

It is another object of this invention to provide a latent fingerprint lifting and recordation device having the provision for proper recordation of all associated information related to the fingerprint which is permanently viewably displayed on the device.

It is still another object of this invention to provide a latent fingerprint lifting and recordation device which will as easily useable and adoptable by law enforcement as a more simple and economical means than that currently in use for lifting latent fingerprints, but which lack any substantial aspects of permanency and professional display of critical evidence for later legal use.

Yet another object of this invention is to provide a latent fingerprint lifting and recordation device which prevents the crime scene investigator from inadvertently touching the sticky surface of the tape and prevents the tape from wrinkling and sticking to itself.

In accordance with these and other objects which will become apparent hereinafter, the instant invention will now be described with reference to the accompanying drawings.

DETAILED DESCRIPTION OF THE INVENTION

Figure 1:
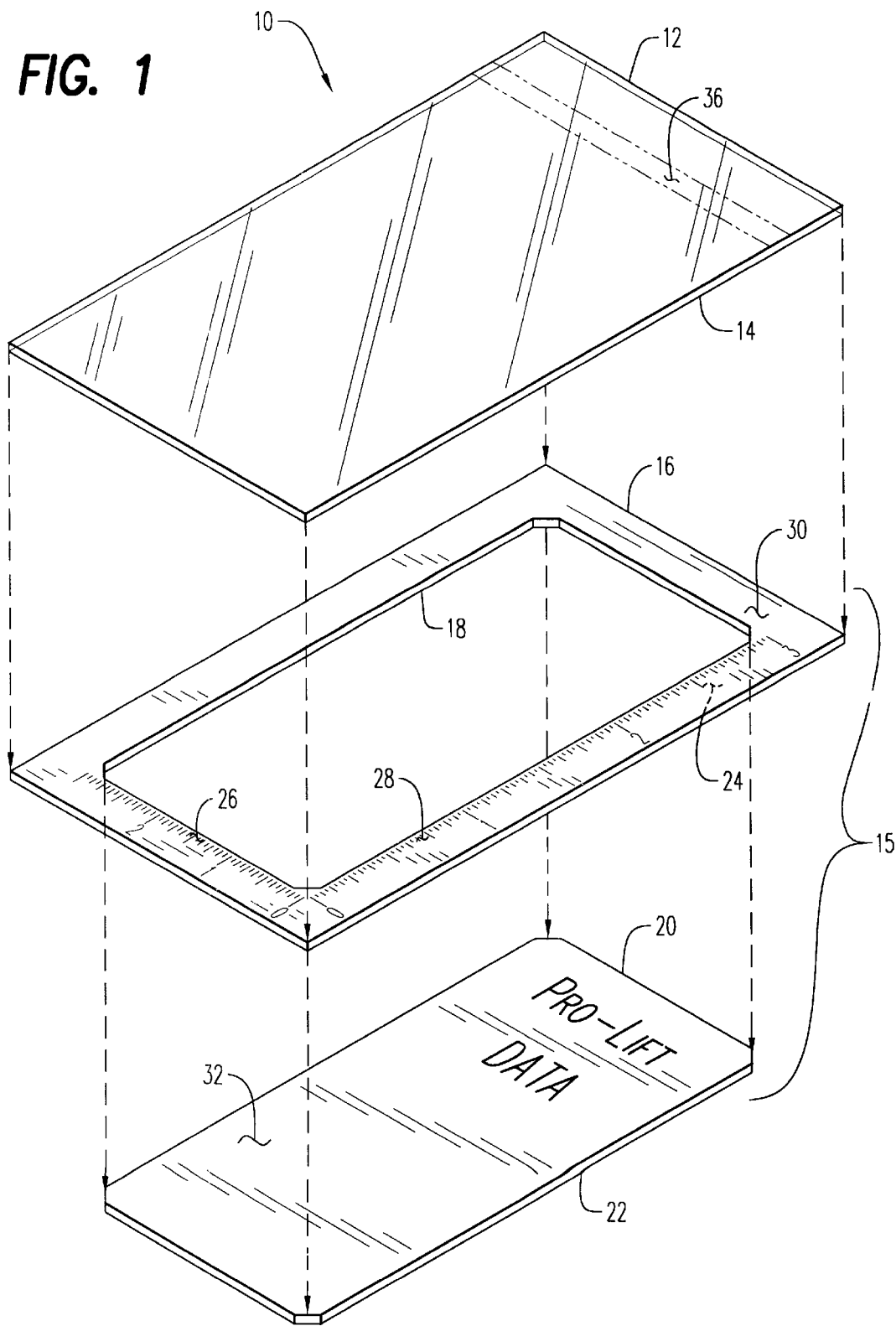
FIG. 1 is an exploded perspective view of the invention.
Figure 2:
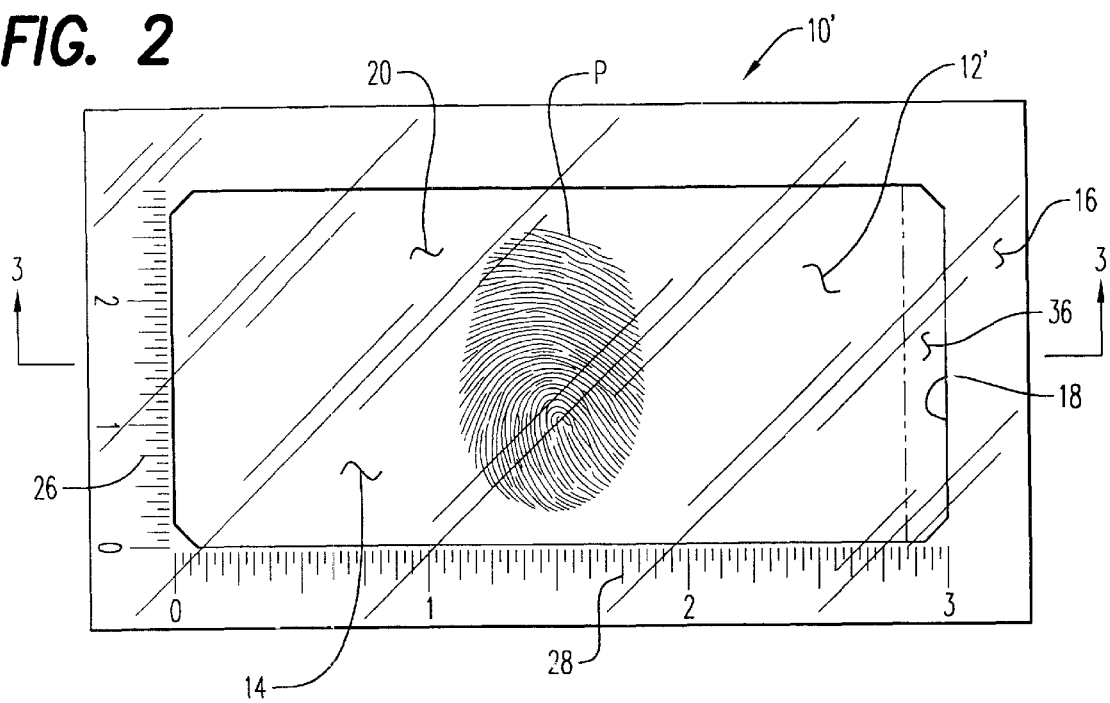
FIG. 2 is a top plan view of the invention after a latent fingerprint has been lifted and recorded.
Figure 3:
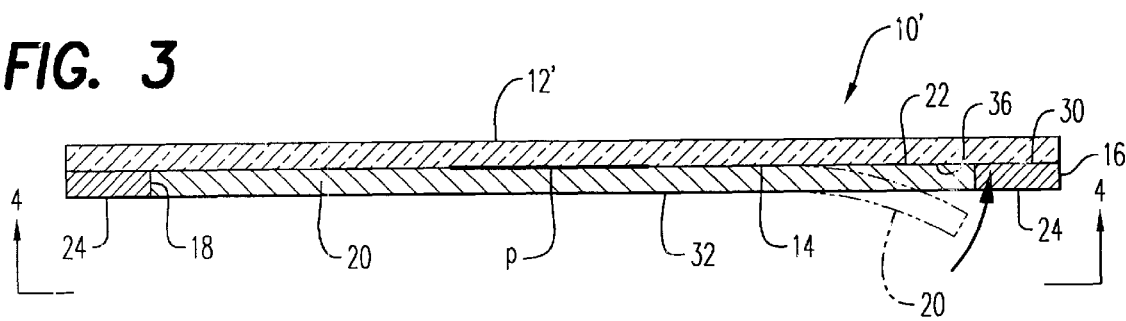
FIG. 3 is a section view in the direction of arrows 3—3 in FIG. 2.
Figure 4:
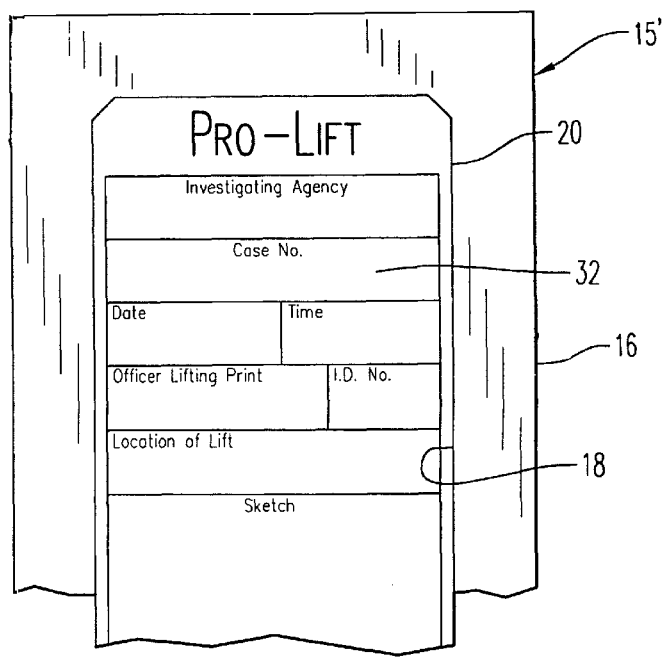
FIG. 4 is a broken view in the direction of arrows 4—4 in FIG. 3.

Referring now to the drawings, the invention is shown in FIG. 1 generally at numeral 10 prior to use and at 10' in FIGS. 2, 3 and 4 after being used to lift a fingerprint P and includes a rectangular flexible transparent fingerprint-lifting sheet 12 having an adhesive surface 14 on one side thereof. The adhesive surface 14 is adhered against a less flexible rectangular opaque sheet 15 formed of heavy paper or plastic having removable central rectangular protective cover 20 which, when removed, leaves an opening 18 formed through a perimeter frame 16. The margins of the transparent sheet 12 and the perimeter frame 16 are substantially similar.

There is full adhesive attachment between the mating surfaces 30 and 32 of the frame 16 and the protective cover sheet 20, respectively, and the adhesive surface 14. The adhesive surface 14 is a strong adhesive, but is releasable from the obverse surface 32 of cover 20.

As best seen in FIG. 2, the obverse surface 30 of the perimeter frame 16 includes distance scales 26 and 28 extending along the respective orthogonal margins of the central opening 18 so that there is a convenient means for assessing the overall size of a latent fingerprint P as it appears in FIG. 2.

The obverse surface 32 of the protective cover 20, as seen in FIG. 4, includes provision for recording important data associated with each latent fingerprint P which has been lifted and appears on the obverse surface of the device 10' as shown in FIG. 2. The printed indicia for entry of this data is directed to such items as the agency that took the fingerprint, a reference number, the officer conducting the investigation and other pertinent information, including the location where the latent fingerprint was found and taken. Note that the reverse surface 22 is preferably plain or unmarked for the purpose described herebelow.

Figure 5:
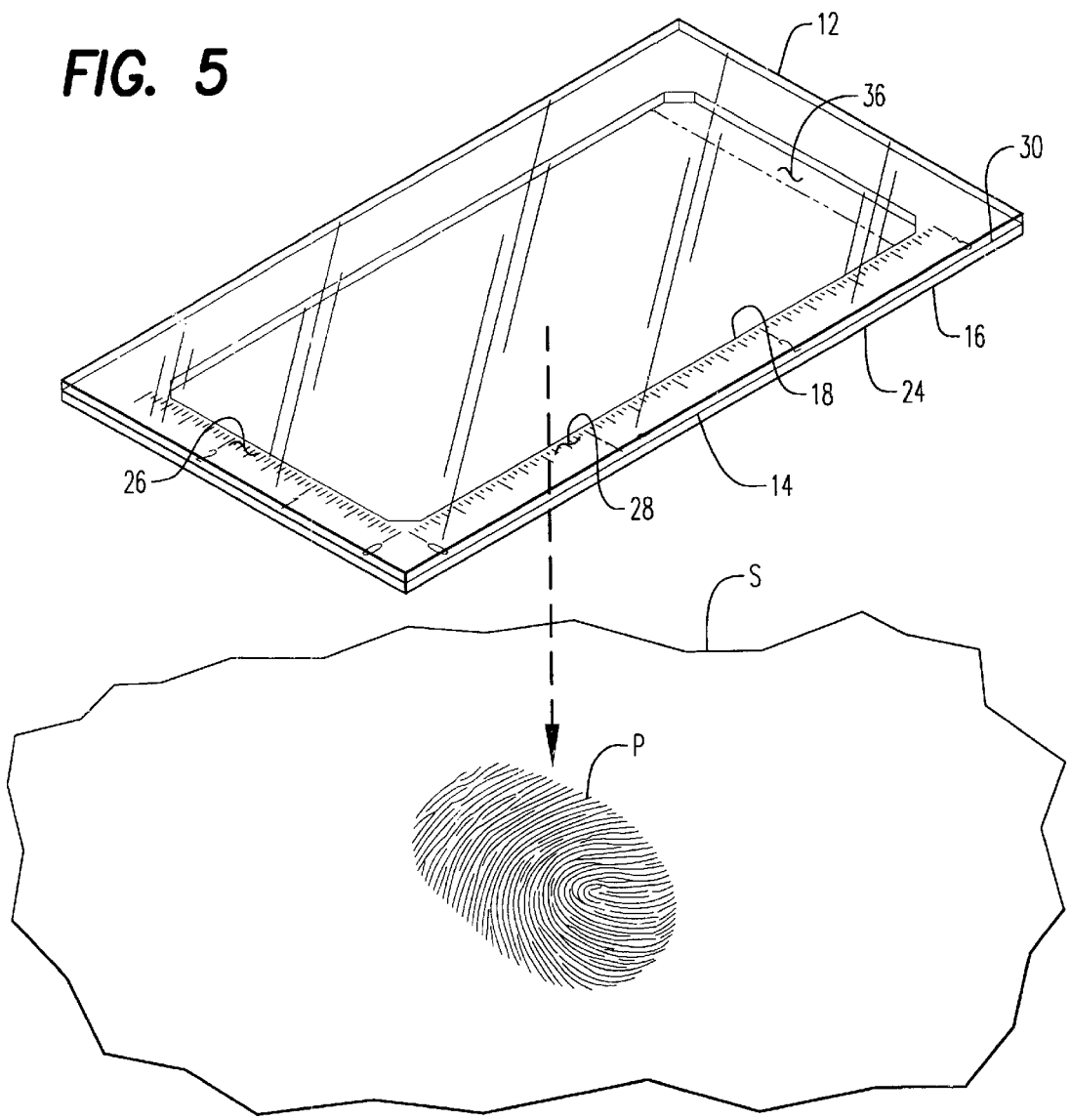
FIG. 5 is a perspective view of the invention absent the protective cover and shown in a position ready to lift a latent fingerprint from a substrate.

To use the device 10, the perimeter frame 16, carrying the adhesive sheet 12, is separated from the protective cover sheet 20. A small strip 36 of the adhesive surface 14 is coated with a non-adhesive coating such as varnish which facilitates easy start-up separation of one end of the protective cover 20. Once the protective cover 20 is separated from the perimeter frame 16 and adhesive sheet 12, as best seen in FIG. 5, the two-part arrangement may be applied and pressed over a viewably enhanced or imaged fingerprint P which has been enhanced by conventional methods such as the application of powder. The imaged latent fingerprint P becomes permanently attached to the adhesive surface 14 in a central location so that it may be viewable within or through the opening 18 of frame 16, again as best seen in FIG. 2.

A further benefit to the perimeter frame 16 and the added rigidity provided thereby is the prevention of the adhesive sheet 12 from inadvertently folding or wrinkling and becoming attached to itself as is likely the case using other conventional adhesive tape means for lifting fingerprints. Moreover, the crime scene investigator is substantially less likely to inadvertently touch the sticky surface of the adhesive sheet 12 and thereby render it useless. Details of material preference are described herebelow.

REVERSAL OF PROTECTIVE COVER

Before the protective cover 20 is reattached to the adhesive surface 14, certain data is entered onto the obverse surface 32 thereof. Although the protective cover 20 may be readhered against adhesive surface 14 by placing the obverse surface 32 thereagainst so that the data area is viewable simultaneously with the fingerprint P, it is preferred that the protective cover 20 be reversed so that the plain reverse surface 22 is placed against the adhesive surface 14. In this preferred orientation, the plain opaque surface 22 serves to viewably enhance the latent fingerprint P and allows the data displayed on the obverse surface 32 to now appear on the reverse surface of the device 10'.

The manufacturing benefit of the preferred embodiment as shown is now more clearly understood. All of the printed information is applied at manufacture to a single obverse surface 30/32 of the opaque sheet 15. This printed information includes the scales 24 and 26 which are applied to what will become the obverse surface 30 of perimeter frame 16 and the data receiving area of obverse surface 32 which becomes the protective cover 20 when removed from adhesive attachment from the adhesive surface 14. Manufacturing techniques for this type of product generally wherein a one-sided adhesive sheet is attached to an opaque or paper type sheet of substantially greater thickness are sufficiently sophisticated to cut through the flexible opaque cover 15 to define opening 18 and thus the margins of the protective cover 20 without cutting through the transparent adhesive sheet 12.

The sequence of manufacture of the present invention 10 is thus to first print the scale and data taking indicia onto the obverse surface 30/32 of the flexible opaque sheet 15, then attach the obverse surface 30/32 to the adhesive surface 14 and thereafter to die cut the margins of the opening 18/ protective cover 20. Packaging of selected numbers of the device 10 may then be completed.

Stock material selection for two-sheet construction of the present invention is made somewhat more economical as well by the above-described invention. Flexible transparent one-sided adhesive material, for example, is preferably formed of stock material having a thickness in the range of 0.0025" (2.5 mils), while the somewhat stiffer, semi-flexible opaque sheet 15 is formed of 0.012" (12 mils), the combined thickness of the device 10 being approximately 0.015" (15 mils). The preferred embodiment of the opaque sheet 15 is an 8 pt. board stock having a thin film applied over both surfaces which is over-laminated with a 0.002" (2 mil.) polyester film for enhanced durability and to facilitate releasable attachment from the adhesive surface 14.

Although the invention 10 is as described herein as being typically applicable to a single fingerprint, the overall size, length and width, may be easily be varied within the scope of this invention so that a complete set of prints, a palm print, or other latent indicia of hand or foot identification may be lifted onto the adhesive surface of the transparent sheet supported by the flexible frame attached around the perimeter thereof.

While the instant invention has been shown and described herein in what are conceived to be the most practical and preferred embodiments, it is recognized that departures may be made therefrom within the scope of the invention, which is therefore not to be limited to the details disclosed herein, but is to be afforded the full scope of the claims so as to embrace any and all equivalent apparatus and articles.

What is claimed is:

1. A latent fingerprint lifting and recordation device of the type which provides a permanent and official fingerprint document, said device comprising:

a flexible transparent latent fingerprint lifting sheet having one adhesive surface thereof;

an opaque semi-flexible sheet substantially similar in size and shape to that of, and adhered in generally coextensive fashion on one surface thereof, to said fingerprint lifting sheet;

a releasable protective cover and a perimeter frame of said opaque sheet defined by a substantially continuous cut formed through, and adjacent side margins of, said opaque sheet but not through said lifting sheet;

whereby, when said fingerprint lifting sheet with said perimeter frame adhesively attached thereto are separated from said cover, an imaged latent fingerprint may be lifted and recorded on said adhesive surface, the latent fingerprint thereafter protectively sandwiched for viewing through said fingerprint lifting sheet when said cover is adhesively reattached to said adhesive surface to form a permanent fingerprint document;

said perimeter frame including scale measurement indicia printed thereon positioned adjacent to the latent fingerprint on said fingerprint lifting sheet.

2. A latent fingerprint lifting and recordation device as set forth in claim 1, wherein:

an obverse surface of said protective cover includes printed information recordation data related to the latent fingerprint taken on said fingerprint lifting sheet.

3. A latent fingerprint lifting device of the type which provides a permanent and official fingerprint document, said device comprising:

a flexible flat transparent sheet having one adhesive surface thereof of a type capable of lifting an imaged latent fingerprint;

a flat opaque sheet having a perimeter frame and a protective cover, said opaque sheet adhered in generally coextensive fashion against said adhesive surface;

said protective cover and said perimeter frame defined by a cut formed substantially continuously adjacent margins of said opaque sheet through said opaque sheet, but not through said transparent sheet;

whereby, when said transparent sheet with said frame adhesively attached thereto are removed from said cover, a latent fingerprint may be lifted and recorded on said adhesive surface, the latent fingerprint thereafter protectively sandwiched for viewing through said transparent sheet when said cover is adhesively reattached to said adhesive surface to form a permanent fingerprint document;

said adhesive surface including a non-adhesive edge portion which facilitates starting the removal of said protective cover from said adhesive surface.

4. A latent fingerprint lifting and recordation device as set forth in claim 3, wherein:

said perimeter frame includes scale measurement indicia printed thereon for size comparison to the latent fingerprint on said fingerprint lifting sheet.

5. A latent fingerprint lifting and recordation device as set forth in claim 4, wherein:

an obverse surface of said protective cover includes printed information recordation data related to the latent fingerprint taken on said fingerprint lifting sheet.

* * * * *